United States Patent
Gruber et al.

(10) Patent No.: US 8,729,038 B2
(45) Date of Patent: May 20, 2014

(54) DOWN REGULATION OF THE GENE EXPRESSION BY MEANS OF NUCLEIC ACID-LOADED VIRUS-LIKE PARTICLES

(76) Inventors: Jens Gruber, Amsterdam (NL); Wolfgang Lüke, Münster (DE); Gabriele Jansen, legal representative, Münster (DE)

( * ) Notice: Subject to any disclaimer, the term of this patent is extended or adjusted under 35 U.S.C. 154(b) by 991 days.

(21) Appl. No.: 12/678,150

(22) PCT Filed: Sep. 12, 2008

(86) PCT No.: PCT/EP2008/007580
§ 371 (c)(1),
(2), (4) Date: Sep. 26, 2011

(87) PCT Pub. No.: WO2009/036933
PCT Pub. Date: Mar. 26, 2009

(65) Prior Publication Data
US 2012/0046340 A1 Feb. 23, 2012

(30) Foreign Application Priority Data
Sep. 14, 2007 (EP) .................................... 07018130

(51) Int. Cl.
*C12N 15/11* (2006.01)
*C07H 21/04* (2006.01)
*A01N 63/00* (2006.01)

(52) U.S. Cl.
USPC ........ 514/44 A; 536/24.5; 424/93.2; 424/93.6

(58) Field of Classification Search
USPC ...................................... 536/24.5; 514/44 A
See application file for complete search history.

(56) References Cited

U.S. PATENT DOCUMENTS

| | | | |
|---|---|---|---|
| 7,666,408 B2 * | 2/2010 | Bachmann | .................. 424/93.6 |
| 2003/0044961 A1 | 3/2003 | Luke et al. | |
| 2004/0166091 A1 * | 8/2004 | Brough | ........................ 424/93.2 |
| 2005/0266020 A1 | 12/2005 | Boehm et al. | |
| 2006/0222662 A1 * | 10/2006 | Hess et al. | .................. 424/204.1 |
| 2009/0226525 A1 * | 9/2009 | de Los Rios et al. | ......... 424/489 |
| 2009/0298955 A1 * | 12/2009 | Handa et al. | .................. 514/773 |

FOREIGN PATENT DOCUMENTS

| | | |
|---|---|---|
| EP | 0 962 525 | 12/1999 |
| EP | 1 270 586 | 1/2003 |
| WO | WO 99/36545 | 7/1999 |
| WO | WO 01/32851 | 5/2001 |
| WO | WO 2006/119096 | 11/2006 |
| WO | WO 2007/064971 | 6/2007 |

* cited by examiner

*Primary Examiner* — Brian Whiteman
(74) *Attorney, Agent, or Firm* — Saliwanchik, Lloyd & Eisenschenk

(57) ABSTRACT

The present invention relates to compositions of virus-like particles for the introduction of RNA-interference (RNAi-) inducing molecules into eukaryotic cells and methods for the cell type-specific transduction of a plurality of eukaryotic cells with RNAi-inducing molecules. The present invention furthermore relates to methods for a diagnosis, prevention and/or treatment of diseases or disease states associated with an increased expression rate of at least one endogenous gene, and/or with the undesired expression of at least one endogenous gene and/or foreign nucleic acids, in particular viral nucleic acids.

32 Claims, 6 Drawing Sheets

Figure 1:
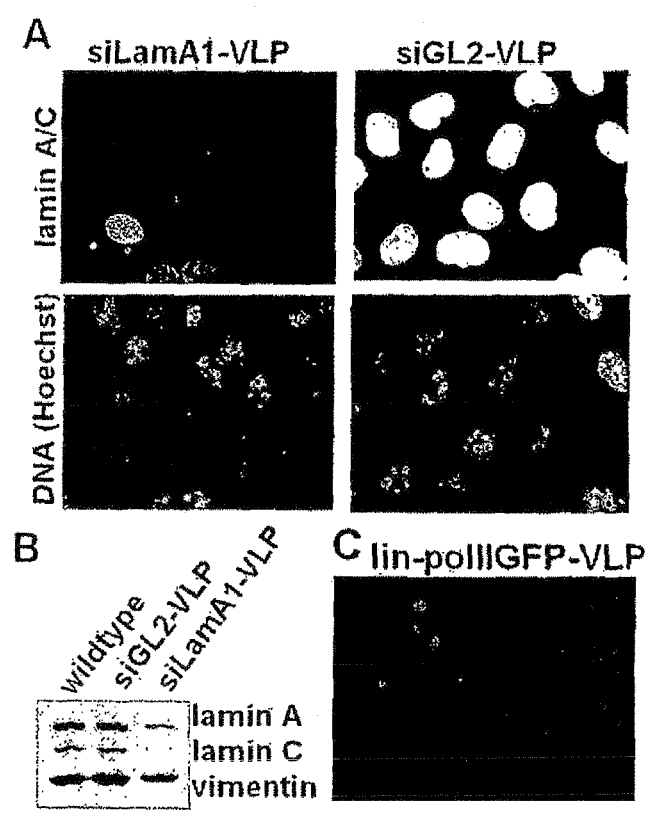

A  Homogenous distribution of fluorescent labelled siRNAs in cytoplasm cross sections (x axis)

B  PEI-VLP 5uM siEme    PEI-VLP 5uM siGL2 emerin   DNA            emerin   DNA

C emerin

A
JCV  wild type  MAPTKRKGERKDP (Amino acids 1-13 of SEQ ID NO:1)

Mut2       MAPTKRKGECPGAAPKKPKDP (Amino acids 1-21
                                       of SEQ ID NO:4)

SV40           MAPTKRKGSCPGAAPKKPKEP (SEQ ID NO:5)
BKV            MAPTKRKGECPGAAPKKPKEP (SEQ ID NO:6)

B

C

DOWN REGULATION OF THE GENE EXPRESSION BY MEANS OF NUCLEIC ACID-LOADED VIRUS-LIKE PARTICLES

CROSS REFERENCE TO A RELATED APPLICATION

This application is a National Stage Application of International Application Number PCT/EP2008/007580, filed Sep. 12, 2008; which claims priority to European Patent Application No. 7018130.0, filed Sep. 14, 2007; which are incorporated herein by reference in their entirety.

The present invention relates to compositions of virus-like particles for the introduction of RNA-interference (RNAi-) inducing molecules into eukaryotic cells and methods for the cell type-specific transduction of a plurality of eukaryotic cells with RNAi-inducing molecules. The present invention furthermore relates to methods for a diagnosis, prevention and/or treatment of diseases or disease states associated with an increased expression rate of at least one endogenous gene, and/or with the undesired expression of at least one endogenous gene and/or foreign nucleic acids, in particular viral nucleic acids.

Gene-therapeutic methods that are currently known are based on the transfection of cells with DNA-constructs encoding for a desired gene product, mostly a therapeutically effective protein. Methods that are used hereby are usually adapted to in vitro methods. A targeted, i.e. selective, transfection of specific cell types without a prior isolation of the cells from their natural environment can not be realized with most of the methods of the state of the art, such as, for example, electroporation or liposome transfection.

Methods for a tissue specific DNA-transfer in vivo so far rely on viral transfer systems. Nevertheless, due to the potential danger of recombination with cellular sequences, these bear a safety risk that can hardly be calculated. A repeated in vivo-application of adenoviruses and adeno-associated viruses, the systems that are currently preferred for the transport of therapeutic genes, is impossible because of their high immunogenicity in most patients. In addition, due to the complex structure of the adenovirus and the structure of the adenoviral genome it is only possible with considerable effort to provide therapeutic DNA at the target site to a sufficient extent and in a suitable form.

Particularly in view of an undesired recombination and the associated danger to permanently modify the genome, gene-therapeutic methods could not be considered for the treatment of transiently occurring disease states, such as, for example, acute infections. Non-viral systems, such as, for example, liposomes and DNA-condensating molecules, indeed avoided these disadvantages, but, in turn, similar to retroviral systems exhibited much lower transfer efficiencies and target cell specificities.

Therefore, there is a need to provide clinically applicable gene-therapeutic compositions and methods, in order to avoid these problems.

It was the object of the present invention to provide compositions, which, while simultaneously maintaining the integrity of the cellular genome of a target cell, allow for a cell type specific introduction of gene-therapeutically effective molecules into eukaryotic cells with high efficiency both in vivo and in vitro. It was a further object of the present invention to provide highly efficient methods for the treatment of pathogenic infections, or for the therapy and/or diagnosis of disease symptoms that are associated with a modified gene expression.

According to the present invention, these objects were solved by a composition comprising a virus like particle ("virus like particle"; VLP) that is composed of several molecules of at least one viral capsid protein, characterized in that at least one RNA-interference (RNAi-) inducing molecule is included in the VLP. After the transfer into the target cell, the RNAi-inducing molecules cause an effective down-regulation of the expression of a gene of interest.

RNA-interference (RNAi) is an evolutionary conserved mechanism for down-regulating the expression of one or several genes ("gene silencing"). A plurality of eukaryotic organisms are able to protect themselves by means of RNAi against viruses and the expression of transposon elements. The principle of the down-regulation of gene expression by means of RNAi is on the one hand based on the sequence specific degradation of the RNA, in particular mRNA, that is generated by the transcription of a target gene, based on an interaction of the transcript with short RNA-molecules comprising, for example, 21-28 nucleotides, so-called small interfering RNA-molecules ("small interfering RNA", siRNA). Catalyzed by the RNase III Dicer, the targeted degradation of an mRNA-molecule first begins with the formation of double-stranded siRNA-molecules from precursor molecules, and a subsequent processing of these molecules, followed by the hybridization of one strand of the double-stranded siRNA with the mRNA-molecule, forming a double-stranded siRNA-mRNA hybrid molecule. Subsequently, a cleavage of the mRNA inside the region as hybridized with the siRNA takes place. This cleavage or hydrolysis, respectively, first occurs endonucleolytically, e.g. catalyzed by the endonuclease argonaute 2 of the RISC-complex. Finally, the cleavage products thus generated are hydrolyzed by exonucleases of the RISC-complex. As a cause of the targeted degradation of mRNA-transcripts, the expression of the target gene is at least partially suppressed.

On the other hand, the expression of a gene can also be down-regulated on the translational level. The effector molecules that are responsible for this are designated as microRNA (miRNA), which, starting from a hairpin structure ("hairpin") of a precursor-RNA, are formed through several processing steps involving the endonucleases Drosha, Pasha, and Dicer. Because of their partial complementarity with the target-mRNA, miRNAs inhibit the translation thereof.

Studies on cell cultures have shown that also exogenously provided siRNA or miRNA, respectively, can induce an RNA-interference in eukaryotic cells, e.g. mammalian cells, including human cells. Because of the low transfer efficiencies, previous methods for introducing RNAi-inducing molecules into eukaryotic cells do not, or only to a very limited extent, allow for a use of this mechanism as a therapeutic approach for the treatment of infections with pathogenic viruses or for the treatment of diseases that are associated with a modified gene expression.

An RNAi-inducing molecule shall mean those RNA-molecules, wherein at least one polynucleotide strand has a sequence that is sufficiently complementary to a target-RNA, preferably a target-mRNA, in order to cause its processing, i.e. its degradation. In order to be RNAi-inducing it is required that the complementarity between RNAi-inducing molecule and a region of the target-RNA is sufficient in order to effect hybridization and a subsequent processing. For example, the complementarity is at least 80%, preferably at least 90%, and most preferred at least 99%, wherein at the 5'- and/or 3'-ends and at the overhangs of an RNAi-effector molecule also nucleotides can be present which are not complementary to the target-RNA.

In order to induce RNAi, several routes can be followed. Thereby, the direct transfer of effector molecules, i.e. siRNA-molecules and/or miRNA-molecules, represents one possibility. An siRNA-molecule shall preferably mean a double-stranded RNA molecule having a length of 19-30 nucleotides, preferably 20-28 nucleotides and particularly preferred having a length of 21-23 nucleotides of each of the single strands. siRNA-molecules also mean single-stranded RNA-molecules having a length of 19-30 nucleotides, preferably 20-28 nucleotides, and particularly preferred having a length of von 21-23 nucleotides, wherein the single stranded RNA-molecule is complementary to a sequence of a target-RNA, in particular a target-mRNA, to at least 80%, preferably to at least 90%, and in particular to more than 99%, and wherein a binding of the siRNA to the target-RNA effects a sequence-specific degradation. Preferably, the siRNA-molecules have 3'-sided overhangs of 1-3 nucleotides.

MiRNA shall mean single stranded RNAi-inducing molecules having a length of 19-30 nucleotides, preferably 20-28 nucleotides, and particularly preferred having a length of 21-23 nucleotides, which after hybridization with a target-mRNA can effect both the inhibition of the translation, as well as effect the degradation thereof.

Alternatively, it is also possible to provide precursor molecules of the actual effective effector molecules, i.e. precursor molecules of siRNA and/or miRNA, which function as a substrate for the siRNA/miRNA-biogenesis-apparatus of the target cell. These include, for example, RNA-precursor molecules, such as double stranded RNA (dsRNA) or short hairpin RNA-molecules (shRNA), which are processed into siRNA-molecules or miRNA-molecules, respectively, by the endonucleases, such as Dicer, Drosha, and/or Pasha. For this, for example dsRNA-molecules or short hairpin RNA-molecules (shRNA) with a length of more than 27 nucleotides, preferably more than 30 nucleotides to about 100 nucleotides or longer, and most preferably dsRNA-molecules having a length of 30-50 nucleotides can be used.

Besides this, it is also possible to introduce RNAi-inducing molecules into the target cells by means of a DNA-based RNAi-approach. For this, DNA-constructs are created, which encode for dsRNA, shRNA, siRNA and/or miRNA, wherein the encoding elements are under the control of regulatory elements that allow for an expression of the dsRNA, shRNA, siRNA and/or miRNA in the target cell. Examples for such control elements are Polymerase II-promoters or Polymerase III-promoters, such as, for example, U6 or H1.

Surprisingly, using the composition according to the invention it could now be found that most diverse kinds of RNAi-inducing molecules could be introduced into a target cell with an extraordinarily high efficiency in a cell type-specific manner. Thereby, the RNAi-inducing molecules as introduced with the composition according to the invention effect a down-regulation of the expression of a target gene to an extent which now allows for a use of the mechanism of the RNA-interference in the therapy, diagnosis and/or prevention of diseases or diseased states that are caused by the expression of a nucleic acid of a pathogenic organism or by the increased or undesired expression of an endogenous gene. Thereby, it was a completely surprising finding that, using the composition according to the invention, RNA-molecules with a defined secondary structure could be introduced into a cell, wherein the RNA-molecules as introduced function as a substrate for the RNAi-biogenesis apparatus of the target cell because of their conformation, so that an efficient down-regulation of the expression of a target gene becomes possible. Thus, with the composition according to the invention, si/miRNA-precursor-molecules such as dsRNA and shRNA can be introduced into a target cell in such a way that they are recognized as a substrate by the si/miRNA generating enzyme complexes in the cell, and are efficiently processed into effector molecules of the sequence specific down-regulation of the expression of a target gene. It was furthermore surprising that even VLP that are derived from DNA-viruses can be used for the transfer of siRNA or miRNA, respectively, into a target cell, or the precursor molecules thereof, such as dsRNA or shRNA.

An RNAi-inducing molecule shall furthermore also include modified RNA-molecules that include 5'-prime and/or 3'-prime modifications, such as fluorescence groups and/or 3'-dTdT-overhangs, and affect a down-regulation of the expression of a gene of interest in a eukaryotic cell.

According to the present invention, an RNAi-inducing molecule shall furthermore mean those RNA-molecules that include analogs of one or several ribonucleotides in the nucleotide sequence and affect a down-regulation of the expression of a gene of interest in a eukaryotic cell. These ribonucleotide-analogs can, for example, increase the structural stability of the RNA-molecule or the stability against ribonucleases. Ribonucleotide-analogs are known to the person of skill and, in comparison with the original RNA-molecules, are modified by base modifications, sugar modifications, e.g. modifications of the 2'-OH group of ribose, and/or phosphate backbone modifications.

Therefore, within the VLP a single type of an RNAi-inducing molecule, i.e. siRNA, dsRNA, shRNA or miRNA or their precursor molecules or DNA encoding can be packaged. Nevertheless, also different types of an RNAi-inducing molecule can be included in a VLP. The RNAi-inducing molecules of the composition according to the invention can be directed against one or several target genes and/or against the same or different sequences of a single target gene.

In this context, the term "directed against a gene" shall mean that an RNAi-inducing molecule contains the sequence information for a sequence specific degradation of an RNA-molecule, preferably an mRNA-molecule of a target gene.

According to the invention, RNAi-inducing molecules can be directed against one or several genes whose expression shall be down-regulated. Preferably the RNAi-inducing molecules of the composition according to the invention are directed against actively expressed genes, whose expression correlates with a pathologic state.

Particularly preferred, the composition according to the invention contains RNAi-inducing molecules that are directed against at least one gene of a pathogen, e.g. a pathogenic virus. Furthermore, the composition according to the invention can contain RNAi-inducing molecules that are directed against at least one endogenous gene, wherein the expression of the endogenous gene and/or the increased expression of the endogenous gene correlates with a pathologic state. Examples for such cellular endogenous genes are, for example, tumor-associated genes, autoimmune-associated genes, metabolic diseases-associated genes, and in particular genes that are associated with neurodegenerative and general neural disease. Additional examples are endogenous genes in the context of infectious diseases (host factors) and genes in the context of dystrophy and progeroid diseases (allele specific, e.g. emerin, lamin A/C, FACE-1, etc.).

The VLP of the composition according to the invention can be composed of one type of a capsid protein or of several different capsid proteins. Preferably, the composition according to the invention contains a VLP that is composed of one type of a capsid protein. Particularly preferably, a VLP is used whose capsid proteins have the inherent property to assemble one with another into a VLP under suitable conditions both in vivo as well as in vitro, i.e. no additional auxiliary factors are required for the formation of the VLP from the monomeric proteins.

The ratio of the mass of VLP to RNAi-inducing molecule is usually found in a range between 1:100 to 100:1, preferably 1:50 to 50:1, particularly preferred 1:20 to 20:1, and most preferred in a range of 1:1 to 20:1.

Preferably, a VLP is used which is free from other components of the authentic virus, such as, for example, authentic viral nucleic acids. Particularly preferred is the use of a VLP which is composed of the capsid protein VP1 of the human JC-virus (JCV). JCV belongs to the genus of polyomaviruses, whose viral genomes are present inside the capsid in the form of double-stranded DNA.

In a particular embodiment, the VLP is composed of recombinantly produced capsid protein. The term "capsid protein" according to the present invention, in addition to the capsid protein of the wild type strain of the respective virus, such as, for example, wild type-VP1, also comprises modified forms of the capsid protein, i.e. proteins that differ from wild type-capsid protein by mutations, such as, for example, substitutions, insertions, and/or deletions. For producing recombinant VP1 preferably a nucleic acid is used that has the sequence as shown in SEQ ID NO. 1, a sequence corresponding to this sequence in the context of the degeneration of the genetic code, or a sequence hybridizing with the sequence under stringent conditions, whereby the nucleic acid sequence or a recombinant vector containing this sequence is introduced into a suitable host cell, the host cell is cultured under conditions whereby an expression of the nucleic acid sequence takes place, and the protein is isolated from the cell or the cellular supernatant. Stringent hybridization conditions are preferably defined according to Sambrook et al. (1989) Molecular Cloning. A Laboratory Manual, Second Edition, Cold Spring Harbor Laboratory Press, and comprise a washing step of 30 min in 0.1×SSC, 0.5% SDS at 68° C.

The amino acid sequence encoded by the nucleic acid according to SEQ ID No.1 is shown in SEQ ID No. 2. In the context of the present invention, preferably a VP1-polypeptide is used containing SEQ ID No. 2 or an amino acid sequence being identical to said sequence to at least 70%, preferably to at least 80%, particularly preferred to at least 90%, and most preferred to at least 95%, wherein the identity is determined over the whole region of SEQ ID No. 2.

In a further preferred embodiment a VP1 protein is used, wherein the amino acid sequence was modified in the N-terminal region, for example in the region of the 25 N-terminal amino acids. In doing so, preferably a heterologous nuclear localization signal is introduced into the amino acid sequence of VP1. Preferred nuclear localization signals contain the amino acid sequence CPGAAP (SEQ ID NO:7)-$X_1X_2P$, wherein $X_1$ and $X_2$ mean arbitrary amino acids and preferably in each case mean K, and, for example, are based on the nuclear localization signals of SV40 or BKV. The amino acid sequences of particularly preferred nuclear localization signals are shown in FIG. 4A.

The nucleic acid sequence encoding for a preferable modified VP1 protein (VP1-Mut2) is shown in SEQ ID No. 3. The corresponding amino acid sequence is shown in SEQ ID No. 4. One object of the present invention thus is a modified JCV-VP1 protein containing a heterologous nuclear localization signal, preferably as mentioned above, a nucleic acid encoding it, and a $VLP_1$ containing at least one accordingly modified VP1 protein, wherein said VLP optionally can contain active agents, in particular nucleic acids, but also other molecules.

Depending from the host/vector system as used, the isolation of recombinant capsid proteins either takes place directly from the host cells and/or from the cell culture supernatant. The advantage of the recombinant method primarily lies in the fact that VLPs can be obtained in a simple fashion with high purity and in large amounts. In practice, in the recombinant synthesis of VP1 the use of baculoviruses together with insect cells, e.g. with the insect cell line Sf 158, has proven its worth as the expression system.

The suitability of the VP1-VLPs as a cell specific DNA-transport and transduction system for cells of renal and neuronal origin was already shown in DE 101 31 145.1. This document furthermore describes a method for the modification of the VP1-VLPs in order to systematically modify their cellular tropism, so that defined target cells and tissues can be selectively transduced.

Surprisingly, it was now found that also RNAi-inducing molecules, in particular dsRNA, shRNA, miRNAs, siRNA or precursor molecules thereof, can be packaged inside a VLP of the JC-virus without changing the structure of these molecules. It was found that RNAi-inducing molecules that induce RNAi in the target cells are sufficiently protected inside of the VLPs both against degradation and structural changes. The term target cells shall mean eukaryotic cells, and preferably the cells of a multi-cellular organism, in particular mammalian cells, including cells of human origin.

For introducing RNAi-inducing molecules into cells corresponding to the natural host spectrum of the virus, whose capsid protein is a component of the composition according to the invention, preferably a VLP is used whose capsid protein corresponds to the wild type capsid protein. For example, the host spectrum of the JCV comprises cells of the neural tissue and cells of neurally-related tissues, such as, for example, oligodendrocytes, astrocytes, and glial cells. When RNAi-inducing molecules shall be introduced into these cells, the composition according to the invention preferably contains a VLP which is composed of the wild type-VP1 capsid protein of the JC-virus.

For providing RNAi-inducing molecules for cells that do not correspond to the natural host spectrum of the virus whose capsid protein is a component of the composition according to the invention, preferably a VLP is used whose capsid protein is modified when compared to the wild type capsid protein. The use of modified VLPs in the composition according to the invention preferably allows for the treatment of diseases that are limited to particular types of cells or to particular tissues, respectively. Particularly preferred, the composition according to the invention consists of a VLP of the JC-virus, wherein at least one capsid protein of the VP1-VLP is modified when compared with the wild type-VP1.

Modifications on the one hand comprise modifications in the amino acid sequence of the wild type capsid protein. In particular insertions, deletions, substitutions and/or fusions with other amino acid sequences belong to this group, with the provisio that the inherent property of the capsid proteins for self assembly, i.e. for forming VLPs, does not get lost. Thus, the VLP of the composition according to the invention can include one or several additional heterologous proteins or parts of the protein in the capsid structure in form of a fusion protein. This means that a heterologous protein or a heterologous part of the protein is anchored in the capsid structure, wherein preferably at least a part of this protein is accessible from the outside. VLPs that are composed of such fusion proteins, because of the fusion part, can interact with a specific surface receptor of the intended target cell. In this way the specificity of the interaction with the intended target cells can be assured and can be adjusted to a multitude of cell types in dependency from the use. It is also possible to limit the tropism of the VLPs to different cells or tissues by a targeted modification of the capsid proteins.

An additional possibility in order to direct the tropism of the VLPs towards a defined type of cell consists in a chemical modification of the VLPs of the composition according to the invention. A chemical modification of the VLPs allows for a flexible use of the composition according to the invention as a transfer system for RNAi-inducing molecules for particular cells or tissues, respectively. For the targeted modification of the target cell specificity of the VLPs, conjugates of VLP and a cell type specific ligand have proven to be advantageous. In a preferred embodiment, at least one ligand is associated with the VLP. Thereby, the ligand basically can be any substance.

The ligand, for example, can be a target cell-specific group, e.g. a binding partner for a cell surface receptor. Suitable examples for binding partners are natural ligands or synthetic analogs thereof, wherein high molecular weight ligands, such as proteins, e.g. transferrin, antibodies or sugars, such as mannose, but also low molecular weight synthetic ligands, e.g. the tripeptide-motif R-G-D (Arg-Gly-Asp), can be used. Alternatively or additionally, also a labeling group, e.g. a group which can be detected using suitable detection methods, such as, for example, a fluorescent labeling group or biotin, can be used as a ligand. Furthermore, the ligand can also be an effector group, e.g. a cytotoxic group. Of course, also combinations of several ligands, in particular combinations of the before-mentioned ligands, can be used.

The interactions between ligand and the capsid protein of the VLP are preferably mediated by chemical anchoring groups. Thereby, in particular the loading of the capsid protein with cationic polymers as anchor molecules for cell specific ligands has proven to be suitable.

Specific examples for cationic polymers are essentially basic amino acid-based polymers, such as, for example, polylysine, in particular poly-L-lysine, etc. Additional specific examples for suitable cationic polymers are polyalkylene amine, polyalkylene imine, preferably poly-$C_2$-$C_4$-alkylene imine, in particular polyethylene imine (PEI), pAMAM (polyamidoamine)-dendrimers and fractionated dendrimers, as well as cationically modified polyethylene glycol. Polyethylene imine is a particularly preferred cationic polymer in the sense of the present invention, since it is non-toxic and has a high density of positive charges. PEI is furthermore able to effect a pH-dependent structural change after uptake into the cells, leading to a destabilization of endosomal and lysosomal cell compartments and thus to a support of the release of RNAi-inducing molecules into the cytoplasm. This process is supported by the pronounced buffer capacity of the imino groups that are protonated in the lysosomes after an acidification and then lead to an osmotic rupture of the vesicular membrane.

The weight ratio of VLP to cationic polymer in the conjugates can be varied within broad ranges. Thus, weight ratios of 5:1 to 1:10 have proven to be suitable, wherein weight ratios of 2:1 and 1:5 are particularly preferred in order to allow for an optimal binding.

Methods for producing conjugates of VP1-VLP and cationic polymers are known from DE 101 31 145.1.

In an additional preferred embodiment, heterologous binding partners or ligands, respectively, e.g. polypeptides or labeling groups, can be coupled directly and with a controllable stoichiometry to the VLPs. The example of a heterobifunctional protein-protein linker is shown in FIG. 5. Here, the amino group of the lysine residue at the outside, preferably of K60 and/or K164, is used in order to bind the linker (here a PEO-maleimide linker) to VP1. Ligands can bind through a cystine residue, e.g. a carboxy-terminal cystine residue, to the second active site of the linker, and give a stable VP1-ligand conjugation which can specifically deliver a VLP-loading into the ligand-specific type of cell.

Thus, another object of the invention is a JCV-VP1 capsid protein to which at least one heterologous binding partner, e.g. a polypeptide, is bound through the amino acid residues K60 and/or K164.

An object of the present invention are furthermore compositions comprising (i) a conjugate of a virus-like particle (VLP) being composed of several molecules of at least one viral capsid protein and at least one cell type specific ligand, wherein VLP and ligand are connected to each other by anchoring groups, such as, for example, cationic polymers or through heterobifunctional linkers, and (ii) RNAi-inducing molecules, that are incorporated into the conjugate of VLP and ligand.

Preferably a VLP is used which is derived from the capsid protein VP1 of the human polyomavirus JC. Preferably, as RNAi-inducing molecules those as described above are used.

For producing a composition according to the preamble of claim 1, the RNAi-inducing molecules, and optionally additional active substances as well as carriers, auxiliary agents, and/or additives are added to the capsid proteins in the desired amounts or concentration, respectively, before and/or during the assembly. In doing so, VLPs can be generated containing RNAi-inducing molecules within the particles. Preferably, the loading of the VLPs with RNAi-inducing molecules takes place during the association of the capsid proteins into the VLP. The packaging of the RNAi-inducing molecules can both occur in vitro as well as in vivo, wherein the incorporation of the RNAi-inducing molecules in das VLP preferably takes place under in vitro conditions. The incorporation of RNAi-inducing molecules into the inside of the capsid coating can take place, e.g. by dissociation (de-assembly) of the capsid coating and a subsequent re-assembly in the presence of the RNAi-inducing molecules or by osmotic shock of the VLPs in the presence of the RNAi-inducing molecules. Furthermore, a target cell specific group that is able to bind with receptors on the surface of a target cell can be bound to the VLP loaded with RNAi-inducing molecules as described above. The conditions for the loading of the VLP are each to be chosen in a way that a degradation or a structural change, respectively, of the RNAi-inducing molecules is avoided.

During packaging, the ratio of capsid-protein-monomer to RNAi-inducing molecules can vary over a brad range, depending from the number of the capsid-proteins per VLP and the size of the molecules to be packaged. The mass ratio of capsid protein to RNAi-inducing molecule usually is found in a range of between 1:100 to 100:1, preferably 1:50 to 50:1, particularly preferred 1:20 to 20:1, and most preferred about 1:1 to 20:1.

Against the background that the capsid-protein is produced recombinantly and separately from the RNAi-inducing molecules in large amounts and with high purity, and that the packing of the nucleic acids, in contrast to the retroviral, adeno-associated or adenoviral vectors, does not take place in packaging cell lines, contaminations with viral nucleic acids and the potential danger of the generation of infectious viruses due to recombination events can be avoided. Since furthermore the packing of RNAi-inducing molecules and the loading of the VLPs with cell specific ligands takes place under defined in vitro conditions, the VLP-RNAi-transfer system, and here in particular the VP1-VLP-transfer system, represents a biologically safe platform technology combining the advantages of viral and non-viral systems, nevertheless, without exhibiting the disadvantages thereof. Thus, the VLPs of the composition according to the invention are particularly characterized by the fact that they are free of nucleic acids of the original virus. Such VLPs, in particular VLPs of recombinant VP1-molecules, are described in WO 97/19174.

The composition according to the invention can be used in order to specifically introduce RNAi-inducing molecules into any type of cells both in vivo and in vitro. Thereby, the targeted transfer of functional RNAi-inducing molecules within a multi-cellular organism leads to a locally limited down-regulation of the expression of a gene of interest by means of RNAi. Thus, when using the composition according to the invention, for example the increased expression of an endogenous gene can be transiently down-regulated, without the existing danger of a modification of the genome of the target cell. Nevertheless, by means of RNAi it is also possible to permanently integrate the genetic information for the targeted, i.e. sequence specific, degradation of RNA, in particular mRNA, into a target cell. Furthermore, the compositions according to the invention can be used in order to down-regulate the expression of undesired genes, for example as the result of a transposition of DNA-segments or a viral infection, in a cell type-specific manner. In particular, the composition according to the invention can be used in order to down-regulate the expression of at least one gene that correlates with a pathological state.

A composition according to the invention can be used in order to treat chronic diseases or their symptoms, respectively. In this case, RNAi-inducing molecules can be used, for example, in the form of DNA-constructs that effect a permanent provision of siRNA or their precursor molecules in a target cell. Furthermore, it now becomes possible using the compositions according to the invention, to transiently establish cell type-specific gene therapies, for example for a treatment of acute infections both in the veterinary as well as in human medicine. The amounts of the composition according to the invention to be administered depend, amongst others, from the kind of disease, the severity of the symptoms, and from the scope of the cells that are affected.

The composition according to the invention can be administered locally or systemically in accordance with known methods for the application of VLPs.

Thus another object of the present invention is a method for introducing RNAi-inducing molecules into a target cell, comprising the steps (i) Assembly of the viral capsid proteins into VLPs in the presence of the RNAi-inducing molecules, and (ii) Contacting the VLP loaded with the RNAi-inducing molecules with the target cell under conditions whereby an uptake of the RNAi-inducing molecules into the target cell can occur.

For modifying the target cell specificity furthermore one or more target cell specific groups can be bound to the VLP as obtained in step (i) that can bind with receptors on the surface of a target cell. The method according to the invention, amongst others, can be used for a down-regulation of at least one gene of interest in a target cell.

Any eukaryotic cell can be used as a target cell. Preferably, the eukaryotic cell is a mammalian cell, and in particular of human origin. Using a composition according to the preamble of claim 1, it is possible to introduce RNAi-inducing molecules both into cells that are present in their natural environment as well as into cells that were isolated from their natural context.

If the target cells, into which the RNAi-inducing molecules shall be introduced, do not correspond to the natural host spectrum of the viruses from which the VLPs that are used in the method according to the invention are derived from, the cell type-specificity of the VLPs can be modified ("re-targeting") before, during or after the loading with RNAi-inducing molecules and, optionally, additional active agents, through complexing of the capsid proteins with ligands as described above. Thereby, advantageously those ligands are selected that can to specifically bind with receptors that are exposed on the cellular surface of the target cells. Alternatively, VLPs can be used for this consisting of capsid proteins which in their amino acid composition include a heterologous protein, which mediates a targeted transfer of RNAi-inducing molecules, and optionally additional active agents, due to its ability to bind to specific receptors on the outer surface of the cell of the target cells.

A further object of the present invention is a pharmaceutical composition comprising VLPs as described above that include RNAi-inducing molecules as described above, for the diagnosis, prevention, and/or treatment of diseases or disease states that are caused by the expression of a foreign nucleic acid, for example a nucleic acid of a pathogenic organism, in particular a pathogenic virus, or by the increased or undesired expression of an endogenous gene.

The present invention furthermore relates to a test kit for introducing RNAi-inducing molecules into any kind of cells or tissues, respectively, comprising VLPs as described above.

Yet another object of the invention are VLP-compositions as indicated above containing other kinds of nucleic acids, e.g. immune-stimulatory nucleic acids, optionally in combination with polypeptide- or peptide-immunogens, aptamers or siDNA-molecules. Further suitable drugs are polar cytostatic agents or toxins.

In addition to the afore-mentioned RNAi-inducing molecules, in particular in the context of infectious retroviral diseases (e.g. HIV-1) also other nucleic acids have to be mentioned as additional therapeutic and prophylactic VLP loadings. For prophylactic uses, immune-stimulatory sequences (ISS) shall be mentioned here, optimally in combination with immunogens from the respective retrovirus (e.g. env-components from HIV-1). In addition, for a therapy a virus inhibition shall be achieved through several non-RNAi inducing nucleic acid sequences. These molecules can be selected from inhibitory DNA and RNA aptamers, as well as from so-called siDNAs that can destroy the genome of retroviruses before the integration thereof into the host genome by a premature activation of the enzyme RNAse H. (Matskevich et al., Aids Res & Human Retroviruses 22 (2006), 1220-1230; Matzen et al. Nature Biotechnology 6 (2007)). Regarding the inclusion of such nucleic acids into VLPs, reference shall be made to the description in connection with RNAi molecules.

The invention is now further explained by the following examples as well as the attached figures and the sequence listing.

EXAMPLE 1

Materials and Methods

Construction and Synthesis of siRNA-Molecules

RNA-oligonucleotides were chemically synthesized and obtained from Dharmacon (Lafayette, Colo.). All siRNA-molecules contained 3'-dTdT-overhangs. Fluorescence labels were coupled to the 5'-end of the sense-strand of the siRNA-molecules, in order to not impart their functionality. Nucleotides (dNTPs) for a PCR were obtained from Boehringer (Mannheim, Germany), PCR-primers and DNA-fragments for producing shRNA by means of in vitro-transcription were provided by NAPS (Gottingen, Germany). Double-stranded RNA having a length of 27 nucleotides (27mer dsRNA) were chemically synthesized and provided by IBA (Gottingen, Germany).

TABLE 1 siRNA-molecules, target genes, positions, modifications

| siRNA | Target gene | Nucleotide position | Modifications | Notes |
|---|---|---|---|---|
| siLamA1 | Human lamin A/C | 608-630 | | |
| siLamA2 | Human lamin A/C | 672-694 | | |
| siL27AC | Human lamin A/C | 670-697 | | Blunt-ended 27mer dsRNA |
| siLamA3 | Human lamin A | 1919-1941 | | |
| siLamA-F | Human lamin A/C | | | Fluorescent dye (fluorescein) is covalently coupled to the 5'-end of the passenger strand |
| siEg5-F | Human Eg5 | 1547-1569 | | Fluorescent dye (rhodamine red) is covalently coupled to the 5'-end of the passenger strand |
| siEme-1 | Human emerin | 628-640 | | |
| siEme-2 | Human emerin | | | |
| siEme-3 | Human emerin | | | |
| siGL2 | Firefly luciferase | 153-175 | | Non-related control |

Antibodies and Indirect Immunofluorescence Microscopy

Transduced cells were treated with −20° C. cold methanol with VLPs 44 hours after the treatment. As primary antibody, a mouse-anti-lamin A/C-antibody (clone 636.23), a mouse-anti-emerin-antibody (Novagen), and a mouse-anti-α-tubulin-antibody (D1H, Sigma, Germany) were used. As secondary antibody, rhodamine- or fluorescein-conjugated goat anti-mouse-IgGs were used. After the fixation, the cells that were washed with PBS were incubated at 37° C. in a humidity chamber for one hour with a first antibody. Subsequently, the cells were washed three times with PBS, and fluorescent secondary antibodies were added for one hour at 37° C. Unbound antibodies were removed by washing three times with PBS, and the DNA was then visualized with 2 µM Hoechst 33342 dye (Hoechst, Germany). For this, the cells were fixed with Mowiol (Hoechst, Germany) on glass slides.

Quantitative Western Blot-Analysis

An SDS-gel electrophoresis was performed according to standard protocols. The proteins were separated by means of standard-SDS-gel electrophoresis, and transferred onto a nitro-cellulose membrane using the semi-dry-transfer method. Membranes were blocked in TBST (20 mM Tris-HCl, 150 mM NaCl, 0.2% Tween 20, pH 7.4), wherein the TBST contained 5% of skim milk powder. Antibodies against lamin A/C, emerin or vimentin were also diluted in TBST, wherein the TBST contained 2.5% of skim milk powder. The accordingly diluted antibodies were incubated with the membrane for 1 h at room temperature. The vimentin protein content was determined in order to allow for an analysis of identical amounts of protein in the Western blot. The membranes were washed twice with TBST, and once with TBST plus 0.5% Triton X-100. Affinity purified horseradish-conjugated porcine anti-mouse immunoglobulins were obtained from Dako (Copenhagen, Denmark). They were diluted 1:10.000 in blocking buffer containing 2.5% of skim milk powder, and incubated with the membrane for 2 h at room temperature. The bands were detected using the ECL-kit (Amersham Biosciences), and quantified on a Lumilmager (Boehringer/Roche, Germany).

Cells

TABLE 2

Cell lines as used in this study

| Cell line | Origin (source) |
|---|---|
| HeLa SS6: | Human cervical carcinoma (ATCC and Gey et al., 1952) |
| MCF-7: | Human breast carcinoma (ATCC and Soule et al., 1973) |
| 293T | Human embryonic kidney (ATCC) |
| COS-7: | Kidney fibroblasts of the African Green Monkey (ATCC) |
| Human Chondrocytes | |
| Glioma SW103 | Human glioblastoma cell line (ATCC) |
| HeLa S3 | Human cervical carcinoma adapted for growth in suspension |
| SupT1 | Human T-cell line (ATCC) |

Adherent cells (i.e. HeLa SS6, MCF-7, 293T. COS-7, chondrocytes and glioma SW103) were cultured in DMEM, which was supplemented with 10% fetal calf serum (FCS) and antibiotics (penicillin and streptomycin, pen/strep). Cells in suspension (i.e. HeLa S3 and SupT1) were cultured in RPMI-1640 high glucose-medium, which was supplemented with 10% FCS and pen/strep.

Production of the VLPs and Loading

The VP1-protein of the polyoma-JC-virus was expressed in insect cells (SF) using a baculoviral system. Secreted protein was isolated from the medium supernatant using gradient centrifugation or ion-exchange-FPLC.

Purified VP1 was present in the form of pentamers and capsids of higher order, therefore, before loading with a nucleic acid these first had to be de-assembled using a de-assembly buffer (10 mM Tris, pH 7.5, 10 mM EGTA, 150 mM NaCl, 5 mM DTT). The loading of the VLPs through re-assembly took place through dialysis of the VP1/nucleic acid mixture against re-assembly buffer (10 mM Tris, pH 7.5, 1 mM $CaCl_2$, 150 mM NaCl) in a micro dialysis setting with an exclusion size of 3.5 kDa over night at 4° C. The standard ratio of DNA to VLP was 1:10 (e.g. 500 ng were added to 5 µg VLP). For the subsequent re-targeting, the re-associated VLPs were mixed with PEI-Tf in a ratio of 1:5 (PEI to VLP, e.g. 1 µg PEI is added to 5 µg VLP).

Transfection/Transduction 24 hours before the treatment with siRNA-loaded VLPs, the cells were each plated in 24-well-plates at 50.000 to 100.000 cells/ml. In case of cells cultured in suspension (i.e. SupT1- and HeLa S3-cell lines), the culture medium was supplemented with 0.5 ng/ml desferiox-amin, in order to stimulate the transferrin metabolism, and to increase the density of the transferrin receptor on the cellular surface. Immediately before the treatment with VLPs, the stimulation medium was replaced by normal culture medium, in order to avoid cytotoxic side-effects of the agent.

Results

Introduction of DNA and siRNA into Human Glioma Cells siRNA loaded VLPs were added to the culture medium of human glioma SW 103-cells. One hour after the treatment, fluorescently labeled siRNAs that were directed against human lamin A/C (siLamA-F) could be observed in the cytoplasm of the glioma cells (see FIG. 1). The specific uptake of exclusively VLP-packaged siRNA was confirmed by a treatment of control cells with naked siRNA, and empty VLPs. 24 hours after the VLP-transduction the cells were examined in view of the RNA-interfering effects by means of indirect immunofluorescence microscopy and Western Blot-analysis.

The amounts of the target protein lamin A/C were effectively down-regulated in the cells treated with siLamA-F-VLP, whereas this could not be observed in the control cells (FIG. 1).

The introduction of siRNA-molecules into glioma SW103-cells was also used in subsequent experiments, including the re-targeting of the VLPs through complexing thereof with PEI-Tf, as a quality control for the packaging of nucleic acids into VLPs.

RNA-Interference in Adherent Cells, Mediated by siRNA-Loaded VLPs Being Complexed with PEI-Tf The VLPs loaded with siRNA-molecules were added to the culture medium of different human cell lines. Several experiments were performed on HeLa SS6-cells. The cells were plated 24 hours before the treatment with the VLPs. The examinations occurred 24 or 48 hours after this treatment.

HeLa-Cells

1. Dosage Dependency and Functional RNA-Interference by PEI-Tf-VLP-Mediated Introduction of siRNA-Molecules.

Figure 2A:
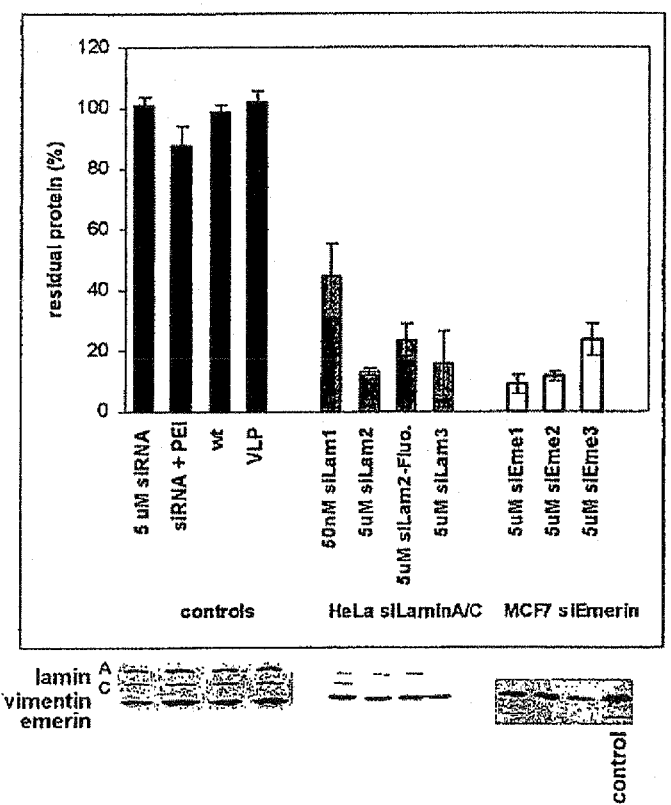
Figure 2B:
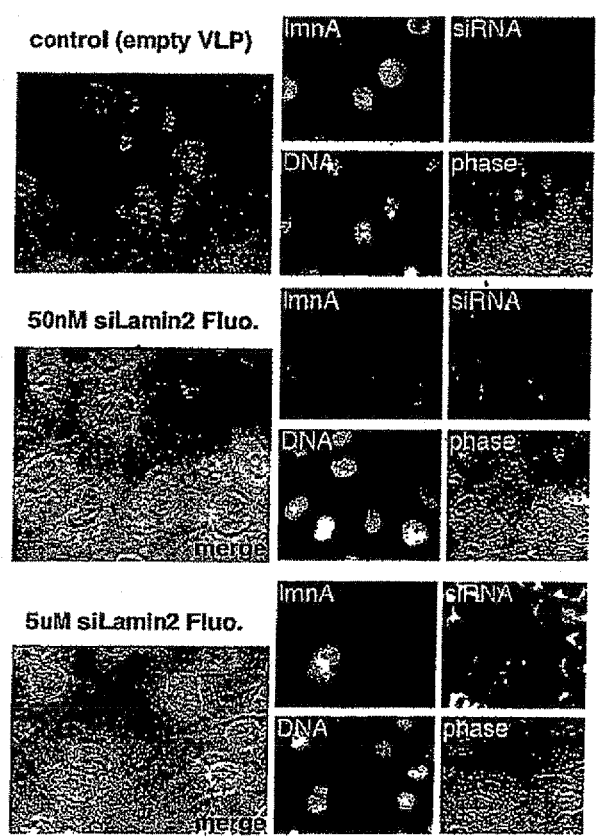

HeLa-cells were plated in 24-well-plates in a density of about 75.000 cells/well, and treated with 1 or 5 µg VLPs after 24 hours. In order to determine the amount of siRNA-molecules that was required for a functional and effective RNA-interference, the VLP were loaded with 50 nM or 3 µM siRNA in reassembly buffer. Empty VLPs, VLP which were loaded with non-related siRNA-molecules, and siRNA-molecules that were only complexed with PEI-Tf served as controls. PEI-Tf were added in a ratio of 1 to 5 (1 µg Pei-Tf:5 µg siRNA-VLP) to the loaded and re-assembled VLP, in order to allow for the uptake into the cells by means of the transferrin receptor. For an efficient RNA-interference in about 100.000 cells of each well of a 24-well-plate, it was necessary to treat these with 5 µg VLP, wherein the VLPs were loaded with 3 µM siRNA (FIG. 2). The transduction of siRNA with VLP that were loaded with 50 nM siRNA, merely led to a small decrease of the target protein lamin A(/C). The uptake of siRNA was confirmed by means of the transduction of fluorescence-labeled siRNA siLamA-F, and the effects of the down-regulation were examined on the protein level by means of quantitative Western Blot-analysis and indirect immunofluorescence microscopy. The transduction of cells with empty Pei-Tf-VLP or with VLP containing a non-related siRNA did not lead to a decrease of the lamin A(/C)-protein content. PEI-Tf complexed siRNA without VLPs caused a weak inhibition of the lamin A(/C)-expression, wherein, nevertheless, the down-regulation was limited to 15-20%, whereas siLamA-PEI-Tf-VLPs caused a nearly complete down-regulation ("knockdown") of the target protein, when used in the suitable concentration (Fig. HeLaA). Three different siRNA-molecules that were directed against lamin A/C, one of which was fluorescence-labeled, were examined on HeLa-cells in order to visualize the uptake of the VLPs into the cells and into the cytoplasm. All siRNA-molecules led to an effective down-regulation of the target protein expression, when they were administered to the cells in the form of PEI-Tf-VLP.

2. Non-Classical 27mer dsRNA-Molecules were Successfully Used for a Down-Regulation Furthermore, a non-classical siRNA, i.e. siL27AC, which consisted of a 5'-phosphorylated dsRNA having a length of 27 nucleotides without 3'-overhangs, was transduced into HeLa-cells, which caused an efficient down-regulation of the expression of the lamin A/C-protein. Thus, the composition according to the invention also makes it possible to introduce substrates for the endonuclease Dicer into the cytoplasm of a target cell by loading of the VLP with a 27mer dsRNA, in order to make it available for the RNA-interference machinery of the cell.

3. PEI-TF VLPs were Used for the Introduction of Active siRNA-Molecules into Breast Cancer Cells A second set of three different siRNA-molecules that were directed against the human emerin-gene was transduced into human breast cancer-MCF-7-cells, as described above. A quantitative Western Blot-analysis showed that all three siRNA-species that were used in these experiments successfully caused a down-regulation of the target gene (FIG. 2A). These results emphasized the broad applicability of the VLPs in view of an efficient transfer of siRNA-molecules which are directed against alternative target genes in different types of cells.

Additional cell lines and information can be taken from Table 3 that reflects a summary regarding nucleic acid transfer experiments using VLPs in different cell lines.

Figure 3:
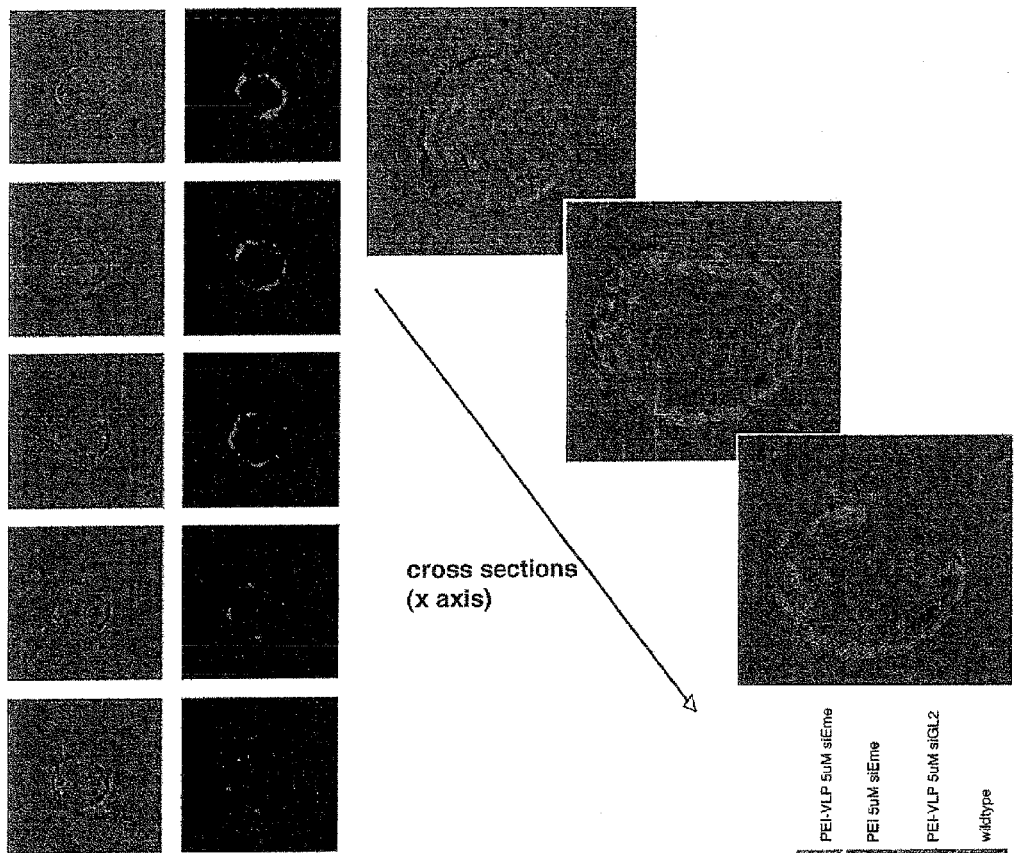
Figure 3:
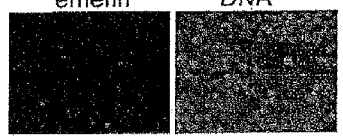
Figure 3:
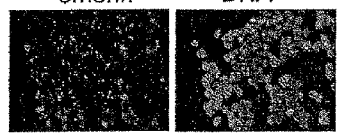
Figure 3:
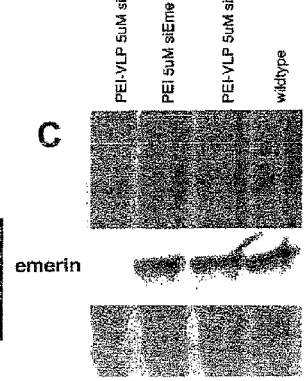
Figure 4:
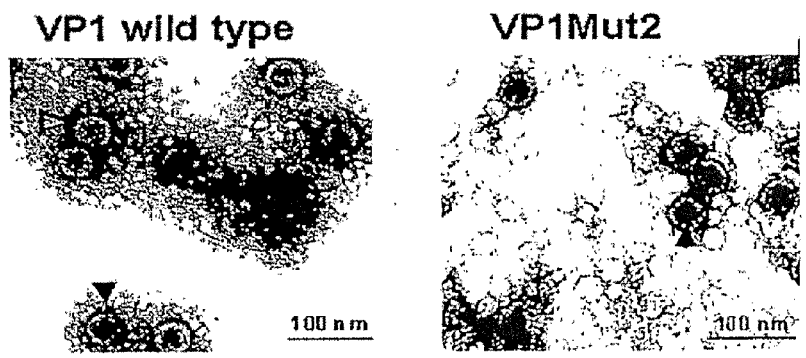
Figure 4:
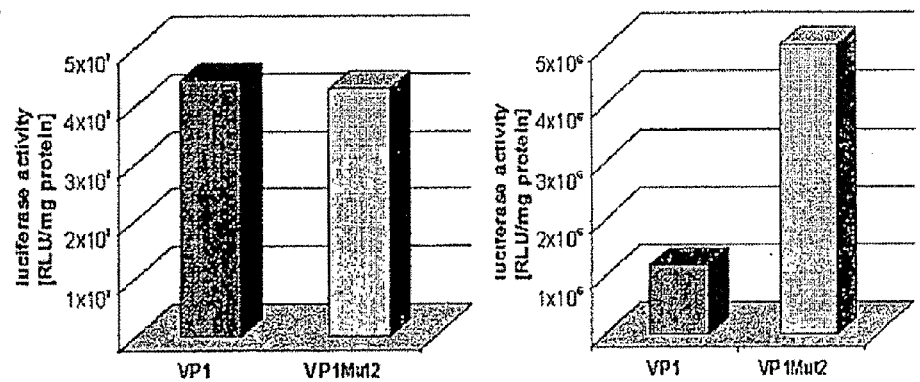
Figure 5:
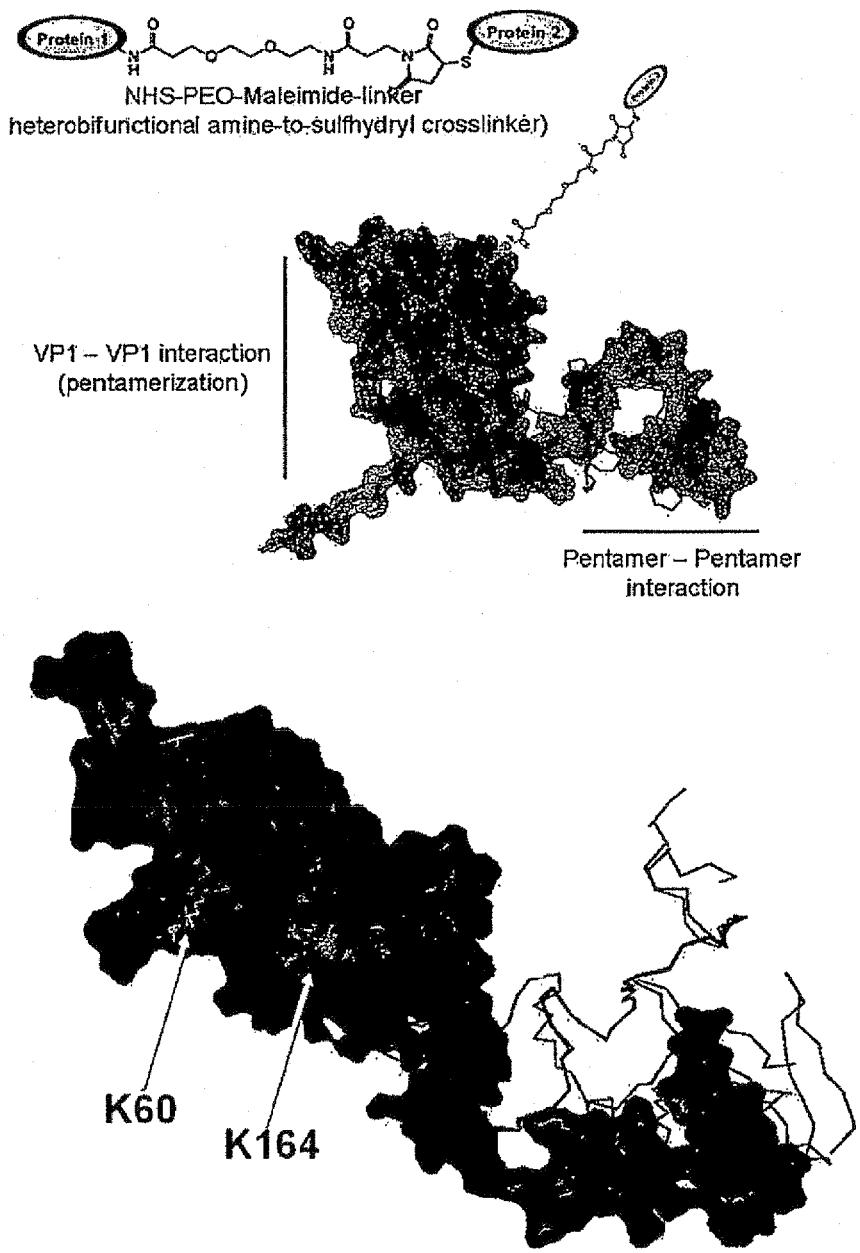

RNA-Interference in Non-Adherent Cells, Mediated by siRNA-Loaded VLPs that are Complexed with PEI-Tf Human SupT1 T-cells were cultured in suspension, and plated out 24 hours before the treatment with VLPs. In order to induce the cellular energy metabolism and to increase the density of the transferrin receptor on the surface of the cells, 15 nM desferrioxamine was added to the culture medium. Immediately before the treatment with VLPs, the medium was replaced by standard culture medium, and the VLPs were added in the amounts as given above. SupT1-cells were transduced with VLP containing siRNA-molecules that were directed against endogenous human emerin, a non-related siRNA (GL2), or no siRNA (FIG. 3). The same VLPs were used as a control with and without PEI-transferrin. As an additional control, cells were subjected to PEI-Tf complexed siRNA-molecules, wherein this RNA was not incorporated into VLPs. In order to show the uptake of the siRNA-molecules into the cytoplasm of the cells, a fluorescence-labeled siRNA was used. Using confocal microscopy, the homogenous dispersion of the fluorescent siRNA in the cytoplasm of SupT1-cells was shown. Sections along the X-axis of such a cell are shown in FIG. 3A. The effective down-regulation of the target gene expression by means of VLP-introduced siRNA was confirmed using indirect immunofluorescence microscopy (FIG. 3B) and Western Blot-analysis (FIG. 3C). The results show a very efficient down-regulation of the emerin-gene expression in nearly 100% of the cells as treated, whereas the treatment with non-related siRNA did not influence the content of emerin. The Western Blot-data showed that a sufficient down-regulation of the emerin could only be achieved, when the cells were treated with siEme-loaded PEI-Tf-complexed VLPs, whereas a PEI-Tf-complexing alone does not lead to a measurable down-regulation of the protein.

Likewise, a VLP-mediated siRNA-uptake was successful, when HeLa S3-cells were used. These cells are adapted to the growth in suspension (data not shown).

TABLE 3

Summary of the experiments, cell lines, siRNA-molecules, RNA- and DNA-constructs, and experimental results.

| Experiment | cell line | SiRNA/target cell | Uptake/ knock-down | Note/Explanation |
|---|---|---|---|---|
| VLP-mediated cellular uptake | HeLa SS6 (human) | siEg5-F siLamA-F | Yes | siRNA-molecules were successfully |

TABLE 3-continued

Summary of the experiments, cell lines, siRNA-molecules,
RNA- and DNA-constructs, and experimental results.

| Experiment | cell line | SiRNA/target cell | Uptake/ knock-down | Note/Explanation |
|---|---|---|---|---|
| of fluorescent siRNA molecules into adherent cells | COS-7 (African Green Monkey) | siEg5-F siLamA-F | Yes | introduced in a dosage dependent manner into the cytoplasm in >90% of the cells as was shown by immuno-fluorescence microscopy, a treatment with PEI alone is not sufficient for an effective introduction of RNAi-inducing molecules into a target cell. |
|  | Chondrocytes (human) | siEg5-F | Yes |  |
| RNAi by means of VLP-introduced siRNA molecules | HeLa SS6 (human) | Lamin A/C (three different siRNA-molecules, one chemically modified, i.e. siLamA1, siLamA2, siLamA-F) | Highly efficient knock-down (>90%) | siRNA-molecules as introduced by means of VLP caused a down-regulation of the expression of a target gene, which is comparable or better than a classical siRNA-transfection (e.g. by cationic liposomes or electroporation). A knock-down was confirmed by means of IIF and Western Blot. In case of the down-regulation of Eg5, the expected secondary effects were found, i.e. a mitotic arrest could be observed in all cells. |
|  |  | siEg5-F | Highly efficient knock-down |  |
|  | COS-7 (African Green Monkey) | siEg5-F | Highly efficient introduction and highly efficient knock-down |  |
|  | Chondrocytes (human) | Lamin A/C (two different siRNA-molecules, siLamA2, siLamA-F) | Knock-down in only a few cells | The cells did not proliferate, which indicates that the experimental timeframe was insufficient for a down-regulation of the protein lamin A, since this protein has a long half-life (a degradation requires one mitosis) |
|  | MCF-7 (human mamma carcinoma) | siEme1, siEme2, siEme3, siLam A1 | Efficient knock-down, documented by Western Blot |  |
|  | 293T (human embryonic kidney) | siEme1 | Efficient knock-down, documented by Western Blot |  |
| RNAi by means of 27mer dsRNA-molecules | HeLa SS6 (human) | siL27A | Efficient knock-down (not shown in IIF and Western Blot) | 27mers of blunt-ended dsRNA-molecules were successfully transduced and processed by Dicer. |

TABLE 3-continued

Summary of the experiments, cell lines, siRNA-molecules,
RNA- and DNA-constructs, and experimental results.

| Experiment | cell line | SiRNA/target cell | Uptake/ knock-down | Note/Explanation |
|---|---|---|---|---|
| Cells in suspension | SupT1 | siLamA-F siEme1 | Uptake (nearly 100%) and functional RNA-interference against emerin (>85% down-regulation) was shown both in IIF and Western Blot. | SupT1-cells require a pre-treatment with desferrioxamine. in order to increase the density of the transferrin receptor. |
| | HeLa S3 | siLamA-F | Uptake was shown | |
| Linear pol II-eGFP-expression construct | SupT1, glioma SW103 | pol II-eGFP linear DNA (2.4 kb) | Introduction into nearly all cells, accordingly, eGFP was expressed in both cell lines | |
| Packaging efficiency | In vitro study | VLP loaded with siRNA | After reassembly, >80% of the VLPs were loaded with si-molecules | |
| Cytotoxic studies | All cell lines/animals | All siRNA, in particular for a therapy | No effects on the vitality of the cells was observed | |

EXAMPLE 2

A modified protein VP1-Mut2 was produced that compared to the wild type sequence had a modification in the amino-terminal region. Because of this modification, the amino acid sequence of a heterologous nuclear localization signal based on the sequence of the viruses SV40 or BKV was introduced. The sequence of the heterologous nuclear localization signal is shown in FIG. 4A.

The chimeric protein VP1-Mut2 was tested for the ability to form intact VLPs, which was confirmed by electron-microscopy imaging. Furthermore, different types of cells were transduced with DNA-loaded VP1-Mut2 VLPs, and in doing so the chimeric form showed at least an equal (COS-7 kidney cells) or up to five-fold increased (SVG glial cells) transduction efficiency. The results are shown in FIGS. 4B and 4C.

EXAMPLE 3

Using a heterobifunctional linker, ligands can be bound directly to the VP1-protein. A preferred embodiment for such a coupling method is depicted in FIG. 5.

DESCRIPTION OF THE FIGURES

FIG. 1: Efficient and functional introduction of siRNA-molecules and DNA into glioma SW 103-cells A) Cells were treated with siLamA1 or siGL2 siRNA-loaded VLPs, and examined 44 hours after the VLP-treatment by means of indirect immuno fluorescence (IIF). The left field shows a group of cells that were treated with siLamA1-VLP, wherein the cells show a nearly complete down-regulation of the target protein (top). The control cells that were treated with the non related control-siGL2-VLP showed a normal lamin A/C-content, wherein lamin A/C is present in the nuclei of the cells. The DNA was stained with Hoechst 33342.

B) The observations from the direct immuno fluorescence microscopy were confirmed with a Western Blot-analysis. Cell extracts of untreated cells or of cells that were treated with siLamA1-VLP or siGL2-VLP were harvested 44 hours after the treatment, and stained with an anti-lamin A/C-antibody. The lamin A/C-content was identical in both control lanes, wherein the portion of lamin A/C in siRNA-VLP-treated populations was markedly reduced. In order to confirm a uniform protein loading, the blots were analyzed in parallel with regard to vimentin.

C) In addition to the siRNA-molecules, a linearized expression construct encoding for eGFP was packaged into VLP and transduced into glioma cells. 24 hours after this treatment nearly all cells showed a positive GFP-expression.

FIG. 2: Qualitative and quantitative documentation of the successful introduction of siRNA by means of modified VLF.

A) The diagram shows the data of a quantitative Western Blot-analysis of three individually performed experiments, wherein siRNA was introduced into HeLa SS6-cells and MCF7-cells using PEI-Tf-VLPs. The treatment of cells with PEI-Tf and siRNA, siRNA alone, empty PEI-Tf-VLPs, and PEI-Tf-VLPs which were loaded with non-related siRNA-molecules, served as individual negative controls. Only the treatment of PEI-Tf and siLamA caused a weak (15-20%) reduction of the content of the target protein, whereas siRNA which was packed into VLPs at an amount of 50 nM already was more efficient. The loading of the VLPs with 5 μM siRNA, and the subsequent complexation with PEI-Tf led to a nearly complete down-regulation of lamin A/C. Other siRNA-molecules that are directed against lamin A/C, one of which was conjugated with and without fluorescein at the 5'-end of the sense strand, showed a comparable effectivity regarding the down-regulation in HeLa-cells. A second set of siRNA-molecules which were directed against human emerin, was examined on MCF-7-cells. As shown by quantitative Western Blot-analysis, in all three cases the siRNA was successfully introduced into the cells. The bottom field shows representative blots after ECL-development. In all cases, vimentin was used as a loading control.

B) A fluorescence microscopy image of HeLa-cells that were treated with siLamA-F-PEI-Tf-VLPs shows the uptake of siRNA-molecules (green) and the dosage-dependent down-regulation of lamin A/C (red). Compared to the higher loading concentrations (bottom field), the effects on the down-regulation of a target gene are weaker, when siRNA is incorporated into VLPs at a concentration of 50 nM (field in the middle). In the control cells, a reduction of the lamin A/C-content can not be observed, when they were treated with VLPs containing non-related siRNA-molecules (top field).

FIG. 3: Transient RNA-interference in human T-cells.

Human Supt1-cells were stimulated with desferrioxamine 24 hours before the treatment with siRNA-loaded PEI-Tf-VLP.

A) A confocal fluorescence microscopy of a single supT1-cell 24 hours after the treatment with VLPs shows a homogenous dispersion of fluorescent siRNA-molecules (siLamA-F) in the cytoplasm. Sections along the Z-axis show that the presence of the siRNA is mainly limited to the cytoplasm, and nearly no fluorescence signal can be observed at the periphery or in the nucleus of the cell.

B) After introduction into the cell, anti-emerin-siRNA-siEme1 clearly showed that this siRNA is available for the RNA-interference machinery of the cell. An indirect immunofluorescence microscopy using anti-emerin-antibodies showed a strong down-regulation of emerin in the siEme-PEI-Tf-VLP-treated population, whereas the emerin content in the control population, which was treated with siGL2-PEI-Tf-VLP, remained unchanged.

C) The results of the immunofluorescence microscopy were confirmed using Western Blot-analysis. Only the siEmei-PEI-Tf-VLP-treated population showed a down-regulation of emerin, whereas the control cells, which were treated with siGL2-PEI-Tf-VLP or empty PEI-Tf-VLP, and the cells, which were only treated with siEmei and PEI-Tf, did not show a reduction of the emerin content. The loading of equal amounts of protein was confirmed by staining of the membrane with Ponceau red (dye is shown in the background).

FIG. 4:

Sequence modifications of the VP1-protein.

A) Comparison of amino terminal sequences of the polyoma JC-virus wild type VP1 and the chimeric VP1-protein (VP-Mut2), which contains a two-part nuclear localization signal due to an amino acid insertion. The sequences as derived from the viruses SV40 and BKV, which formed the bases for the modifications, are shown for comparison.

B) In electron microscopy imaging, the chimeric VP1-protein Mut2 showed the same de- and reassembly characteristics as the wild type VP1-protein.

C) The chimeric VP1-protein Mut2 showed a higher transduction efficiency in SVG-glial cells than the wild type-protein. Following the transduction of a luciferase-expression construct, the relative luciferase-activity was determined.

FIG. 5:

By coupling of ligands to lysine residues of VP1, a retargeting becomes possible. One example for a heterobifunctional linker molecule being able to couple amino to sulfhydryl groups, is shown above. Using this linker molecule (or analogous linker molecules), lysine residues on a first protein (e.g. VP1) and cysteine residues on a second protein (e.g. ligand) can be interconnected. In the middle part of the Figure, the structure of the JCV-VP1 proteins as calculated, and, schematically, the linker molecule when coupled to an accessible lysine residue are shown. At the very bottom, the JCV-VP1-protein is shown in a top view (i.e. from the outside of the capsid). Both lysine residues K60 and K164 that are suitable for a coupling of ligands are indicated. These lysine residues can be used for attaching a heterobifunctional linker molecule as shown above.

The invention claimed is:

1. A composition, comprising a virus-like particle (VLP) wherein said VLP comprises at least one viral capsid protein, and wherein at least one RNA-interference (RNAi-) inducing molecule is included in the interior of the VLP, wherein said VLP comprises at least one viral capsid protein that is modified with a heterobifunctional linker molecule that allows for a retargeting of said VLP, wherein said VLP comprises the capsid protein VP1 of a human polyoma JC virus, and wherein the heterobifunctional linker molecule is bound to at least one lysine residue on said capsid protein VP1 of the human polyoma JC virus, wherein the lysine residue corresponds to K60 or K164 of SEQ ID NO:2.

2. The composition according to claim 1, wherein said RNAi-inducing molecule is an RNA and/or an RNA-analog.

3. The composition according to claim 2, wherein said RNA is siRNA, miRNA, dsRNA, shRNA or a precursor thereof.

4. The composition according to claim 1, wherein said RNAi-inducing molecule is a DNA and/or a DNA-analog, encoding siRNA, miRNA, dsRNA, shRNA or a precursor thereof.

5. The composition according to claim 4, wherein the DNA comprises regulatory elements for expression in a target cell.

6. The composition according to claim 1, wherein the ratio of the masses of VLP to RNAi-inducing molecule is from 1:1 to 20:1.

7. The composition according to claim 1, wherein said VLP comprises the capsid protein VP1 of a human polyoma JC virus.

8. The composition according to claim 1, wherein said VLP is free from other components of an authentic virus.

9. The composition according to claim 1, wherein at least one capsid protein of the VLP is associated with at least one target cell-specific group via one or more heterobifunctional linker molecules.

10. The composition according to claim 9, wherein said target cell-specific group is a ligand that is able to bind to one or more receptors that are presented on the cellular surface of the target cell.

11. The composition according to claim 10, wherein said ligand is a transferrin and said receptor is a transferrin receptor.

12. The composition according to claim 9, wherein said target cell specific group is associated with at least one capsid protein of the VLP by means of one or more chemical linker groups.

13. The composition according to claim 12, wherein said linker group is a cationic polymer.

14. The composition according to claim 13, wherein said cationic polymer is polyethylene imine.

15. The composition according to claim 1, wherein said capsid protein is a fusion protein with a fusion part.

16. The composition according to claim 15, wherein the fusion part of the fusion protein does not interfere with the formation of the VLP.

17. The composition according to claim 15, wherein the fusion part of the fusion protein is able to bind to receptors that are presented on the cellular surface of a target cell.

18. The composition according to claim 1, wherein the VLP comprises a modified capsid protein that has a host spectrum that is not identical to a host spectrum of the unmodified VLP.

19. The composition according to claim 1, wherein said capsid protein of the VLP is recombinantly produced.

20. A method for introducing RNAi-inducing molecules into a target cell wherein said method comprises contacting a target cell with a composition of claim 1.

21. The method according to claim 20, wherein the cell is a mammalian cell.

22. The method according to claim 21, wherein the mammalian cell is of human origin.

23. The method according to claim 20, wherein the expression of at least one gene in the target cell correlates with a pathologic state.

24. The method according to claim 20, wherein the expression of at least one endogenous gene is increased in the target cell.

25. The method according to claim 24, wherein the increased expression of the endogenous gene correlates with a pathologic state.

26. A method for producing a medicament for the diagnosis and/or treatment of a disease or a disease state caused by the expression of a nucleic acid that stems or is derived from a pathogenic organism, or by the increased or undesired expression of an endogenous gene, wherein said method comprises the use of a composition of claim 1.

27. A method for producing a composition according to claim 1, comprising the assembly of the viral capsid proteins into a VLP in the presence of the RNAi-inducing molecules.

28. The method according to claim 27, comprising coupling of a target cell specific group to the VLP that is able to bind to one or more receptors on the cellular surface of a target cell.

29. A method for down-regulating at least one gene in a target cell, comprising the steps:
  (i) providing a composition according to claim 1,
  (ii) contacting of the composition from step (i) with the target cell under conditions that allow for an uptake of the RNAi-inducing molecules into the target cell.

30. A test kit for introducing RNAi-inducing molecules into a target cell, comprising a composition according to claim 1.

31. A pharmaceutical composition comprising VLP and RNAi-inducing molecules according to claim 1, optionally together with one or more buffers, auxiliary agents and additives and/or diluents.

32. A method for the therapy and/or diagnosis of a disease or a disease state caused by the expression of a nucleic acid that stems or is derived from a pathogenic organism, or by the increased or undesired expression of an endogenous gene, wherein said method comprises administering, to a subject in need of such therapy and/or diagnosis, a composition of claim 31.

* * * * *

SEQUENCE LISTING

```
<160> NUMBER OF SEQ ID NOS: 7

<210> SEQ ID NO 1
<211> LENGTH: 1065
<212> TYPE: DNA
<213> ORGANISM: Artificial
<220> FEATURE:
<223> OTHER INFORMATION: Polyoma JC VP1 Gen
<220> FEATURE:
<221> NAME/KEY: misc_feature
<222> LOCATION: (1)..(1065)

<400> SEQUENCE: 1
atggccccaa caaaaagaaa aggagaaagg aaggaccccg tgcaagttcc aaaacttctt        60
ataagaggag gagtagaagt tctagaagtt aaaactgggg ttgactcaat tacagaggta       120
gaatgctttt taactccaga aatgggtgac ccagatgagc atcttagggg tttagtaag       180 tcaatttcta tatcagatac atttgaaagt gactccccaa ataaggacat gcttccttgt       240
tacagtgtgg ccagaattcc actacccaat ctaaatgagg atctaacctg tggaaatata       300
ctaatgtggg aggctgtgac cttaaaaact gaggttttag gggtgacaac tttgatgaat       360
gtgcactcta atggtcaagc aactcatgac aatggtgcag gaaagccagt gcagggcacc       420
```

```
agctttcatt ttttttctgt tgggggggag gctttagaat tacaggggggt ggtttttaac    480 tacagaacaa agtacccaga tggaacaatt tttccaaaga atgcaacagt gcaatctcaa    540
gtaatgaaca cagagcacaa ggcgtaccta gataagaaca aagcatatcc tgttgaatgt    600
tgggttcctg atcccaccag aaatgaaaac acaagatatt ttgggacact aacaggagga    660
gaaaatgttc ctccagttct tcatataaca aacactgcca caacagtgct gcttgatgaa    720
tttggtgttg ggccactttg caaaggtgac aacttgtatt tgtcagctgt tgatgtttgt    780
ggaatgttta ctaacagatc tggtacccag cagtggagag gactgtccag atattttaag    840
gttcagctga gaaaaaggag ggttaaaaac ccctacccaa tttctttcct tcttactgat    900
ttgattaaca gaaggaccccc tagagttgat gggcagccta tgtatggtat ggatgctcag    960
gtagaggagg ttagagtttt tgaggggaca gaggaacttc caggggaccc agacatgatg   1020
agatatgttg acagatatgg acagttgcaa acaaagatgc tgtaa                   1065
```

<210> SEQ ID NO 2
<211> LENGTH: 354
<212> TYPE: PRT
<213> ORGANISM: Artificial
<220> FEATURE:
<223> OTHER INFORMATION: Polyoma VP1
<220> FEATURE:
<221> NAME/KEY: MISC_FEATURE
<222> LOCATION: (1)..(354)

<400> SEQUENCE: 2

```
Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Leu Gly Val Thr Thr Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240
```

Phe Gly Val Gly Pro Leu Cys Lys Gly Asp Asn Leu Tyr Leu Ser Ala
            245                 250                 255

Val Asp Val Cys Gly Met Phe Thr Asn Arg Ser Gly Thr Gln Gln Trp
            260                 265                 270

Arg Gly Leu Ser Arg Tyr Phe Lys Val Gln Leu Arg Lys Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Leu Pro Gly Asp
            325                 330                 335

Pro Asp Met Met Arg Tyr Val Asp Arg Tyr Gly Gln Leu Gln Thr Lys
            340                 345                 350

Met Leu

<210> SEQ ID NO 3
<211> LENGTH: 1089
<212> TYPE: DNA
<213> ORGANISM: Artificial
<220> FEATURE:
<223> OTHER INFORMATION: Polyoma VP1-Mut2
<220> FEATURE:
<221> NAME/KEY: misc_feature
<222> LOCATION: (1)..(1089)

<400> SEQUENCE: 3

```
atggcccaa caaaagaaa aggagaatgt ccagggggcag ctcccaaaaa accaaaggac     60
cccgtgcaag ttccaaaact tcttataaga ggagagtag aagttctaga agttaaaact   120
ggggttgact caattacaga ggtagaatgc tttttaactc agaaatgggt gacccagat   180
gagcatctta ggggttttag taagtcaatt tctatatcag atacatttga aagtgactcc   240
ccaaataagg acatgcttcc ttgttacagt gtggccagaa ttccactacc caatctaaat   300
gaggatctaa cctgtggaaa tatactaatg tgggaggctg tgaccttaaa aactgaggtt   360
ttaggggtga caactttgat gaatgtgcac tctaatggtc aagcaactca tgacaatggt   420
gcaggaaagc cagtgcaggg caccagcttt cattttttttt ctgttggggg ggaggcttta   480
gaattacagg gggtggtttt taactacaga acaaagtacc cagatggaac aatttttcca   540
aagaatgcaa cagtgcaatc tcaagtaatg aacacagagc acaaggcgta cctagataag   600
aacaaagcat atcctgttga atgttgggtt cctgatccca ccagaaatga aaacacaaga   660
tattttggga cactaacagg aggagaaaat gttcctccag ttcttcatat aacaaacact   720
gccacaacag tgctgcttga tgaatttggt gttgggccac tttgcaaagg tgacaacttg   780
tatttgtcag ctgttgatgt tgtggaatg tttactaaca gatctggtac ccagcagtgg   840
agaggactgt ccagatattt taaggttcag ctgagaaaaa ggagggttaa aaacccctac   900
ccaatttctt tccttcttac tgattttgatt aacagaagga ccctagagt tgatgggcag   960
cctatgtatg gtatggatgc tcaggtagag gaggttagag tttttgaggg gacagaggaa  1020
cttccagggg acccagacat gatgagatat gttgacagat atggacagtt gcaaacaaag  1080
atgctgtaa                                                          1089
```

<210> SEQ ID NO 4
<211> LENGTH: 362
<212> TYPE: PRT
<213> ORGANISM: Artificial

```
<220> FEATURE:
<223> OTHER INFORMATION: VP1-Mut2
<220> FEATURE:
<221> NAME/KEY: MISC_FEATURE
<222> LOCATION: (1

```
<212> TYPE: PRT
<213> ORGANISM: Artificial
<220> FEATURE:
<223> OTHER INFORMATION: SV40
<220> FEATURE:
<221> NAME/KEY: MISC_FEATURE
<222> LOCATION: (1)..(21)

<400> SEQUENCE: 5

Met Ala Pro Thr Lys Arg Lys Gly Ser Cys Pro Gly Ala Ala Pro Lys
1               5                   10                  15

Lys Pro Lys Glu Pro
            20

<210> SEQ ID NO 6
<211> LENGTH: 21
<212> TYPE: PRT
<213> ORGANISM: Artificial
<220> FEATURE:
<223> OTHER INFORMATION: BKV
<220> FEATURE:
<221> NAME/KEY: MISC_FEATURE
<222> LOCATION: (1)..(21)

<400> SEQUENCE: 6

Met Ala Pro Thr Lys Arg Lys Gly Glu Cys Pro Gly Ala Ala Pro Lys
1               5                   10                  15

Lys Pro Lys Glu Pro
            20

<210> SEQ ID NO 7
<211> LENGTH: 6
<212> TYPE: PRT
<213> ORGANISM: Artificial
<220> FEATURE:
<223> OTHER INFORMATION: amino acid sequence of preferred nuclear
      localization signal

<400> SEQUENCE: 7

Cys Pro Gly Ala Ala Pro
1               5
```